(12) United States Patent
Osmundsen et al.

(10) Patent No.: US 12,227,473 B2
(45) Date of Patent: *Feb. 18, 2025

(54) PRODUCTION OF GLYCOLALDEHYDE BY THERMOLYTIC FRAGMENTATION

(71) Applicant: HALDOR TOPSØE A/S, Kgs. Lyngby (DK)

(72) Inventors: Christian Mårup Osmundsen, Gentofte (DK); Morten Boberg Larsen, Smørum (DK)

(73) Assignee: HALDOR TOPSØE A/S, KGS. Lyngby (DK)

(*) Notice: Subject to any disclaimer, the term of this patent is extended or adjusted under 35 U.S.C. 154(b) by 156 days.

This patent is subject to a terminal disclaimer.

(21) Appl. No.: 17/821,967

(22) Filed: Aug. 24, 2022

(65) Prior Publication Data

US 2022/0402848 A1    Dec. 22, 2022

Related U.S. Application Data (63) Continuation of application No. 16/332,600, filed as application No. PCT/EP2017/081987 on Dec. 8, 2017, now Pat. No. 11,472,761.

(30) Foreign Application Priority Data

Dec. 8, 2016   (DK) ................................ 2016 00750

(51) Int. Cl.
*C07C 45/60* (2006.01)
*B01J 47/04* (2006.01)
*C07C 45/81* (2006.01)

(52) U.S. Cl.
CPC .............. *C07C 45/60* (2013.01); *C07C 45/81* (2013.01); *B01J 47/04* (2013.01)

(58) Field of Classification Search
CPC ........... C07C 45/60; C07C 45/81; B01J 47/04
See application file for complete search history.

(56) References Cited

U.S. PATENT DOCUMENTS

| | | |
|---|---|---|
| 2,564,820 A | 8/1951 | Pieter |
| 5,397,582 A | 3/1995 | Underwood et al. |
| 7,094,932 B2 | 8/2006 | Majerski et al. |
| 2004/0022912 A1 | 2/2004 | Majerski et al. |
| 2007/0249871 A1 | 10/2007 | Almeida et al. |
| 2010/0160624 A1 | 6/2010 | Cunningham |
| 2015/0337087 A1 | 11/2015 | Zhou et al. |
| 2016/0002137 A1 | 1/2016 | Taarning et al. |
| 2021/0292263 A1 | 9/2021 | Osmundsen et al. |

FOREIGN PATENT DOCUMENTS

| | | |
|---|---|---|
| EP | 0046680 A1 | 3/1982 |
| GB | 616278 A | 1/1949 |
| GB | 633552 A | 12/1949 |
| GB | 2079278 A | 1/1982 |
| JP | H06506361 A | 7/1994 |
| JP | H06509716 A | 11/1994 |
| JP | 2003104929 A | 4/2003 |
| RU | 2371429 C2 | 10/2009 |
| WO | 9217076 A1 | 10/1992 |
| WO | 9303632 A1 | 3/1993 |
| WO | 0240436 A1 | 5/2002 |
| WO | 2016001169 A1 | 1/2016 |

OTHER PUBLICATIONS

Denmark Search Report mailed May 9, 2017 in Denmark Application No. PA 2016 00750 (7 pages).
International Search Report (PCT/ISA/210) mailed on Mar. 2, 2018, by the European Patent Office as the International Searching Authority for International Application No. PCT/EP2017/081987.
Office Action (Text of the First Office Action) issued on Jul. 1, 2021, by the China National Intellectual Property Administration in corresponding Chinese Patent Application No. 201780060926.1, and an English Translation of the Office Action. (10 pages).
Office Action issued Apr. 13, 2021, by the Russian Patent Office in Russian Patent Application No. 201920982/04 (041004) and an English Translation of the Office Action. (21 pages).
Pan, L. et al. "Effects of Metal Salt Additives on Biomass Microwave Pyrolysis Characteristic" Transactions of the Chinese Society for Agricultural Machinery, 2013, vol. 44, No. 6, pp. 162-167. With English Abstract.
Written Opinion (PCT/ISA/237) mailed on Mar. 2, 2018, by the European Patent Office as the International Searching Authority for International Application No. PCT/EP2017/081987.
Zhou, X. et al. "Fast Pyrolysis of Glucose-Based Carbohydrates with Added NaCl Part 2: Validation and Evaluation of the Mechanistic Model" Published on behalf of the AIChE, AIChE Journal, vol. 62, No. 3, Mar. 2016, pp. 778-791.
Office Action (Notice of Reasons for Refusal) issued on Aug. 2, 2021, by the Japanese Patent Office in corresponding Japanese Patent Application No. 2019-530692, and an English Translation of the Office Action, 8 pages.
Essig, M., et al., "Influences of "neutral" salts on thermochemical conversion of cellulose of sucrose", Res. Thermochem. Biomass Convers, 1988, pp. 143-154.
Osmundsen, Christian Mårup, et al., "Catalytic Conversion of Carbohydrates" , Department of Physics Technical University of Denmark, Jan. 1, 2013, retrieved from the internet: http://orbit.dtu.dk/files/54426932/Thesisfinal.pdf.

(Continued)

*Primary Examiner* — Sikarl A Witherspoon
(74) *Attorney, Agent, or Firm* — Boone IP Law (57) ABSTRACT

A process for the production of glycolaldehyde by thermolytic fragmentation of a carbohydrate feedstock including mono- and/or di-saccharide(s) and a system suitable for performing the process. The process and the system are suitable for industrial application, and the process may be performed in a continuous process. The salt-depleted carbohydrate feedstock may include one or more impurities selected from the group of arsenic, lead, sulfate, sulfur dioxide, and 5-(hydroxymethyl)furfural.

19 Claims, 1 Drawing Sheet

(56) References Cited

OTHER PUBLICATIONS

Patwardhan, Pushkaraj R., et al., "Influence of inorganic salts on the primary pyrolysis products of cellulose", Bioresource Technology, 2010, vol. 101, No. 12, pp. 4646-4655.
Schipovskaja, A.B., "Methods of separation of natural polysaccharides and physico-chemical properties thereof", 2015, 8 pages, (with a Partial English translation of document).

PRODUCTION OF GLYCOLALDEHYDE BY THERMOLYTIC FRAGMENTATION

CROSS REFERENCE TO RELATED APPLICATIONS

The present application is a continuation of U.S. application Ser. No. 16/332,600, filed on Mar. 12, 2019, which is a U.S. national stage of International Application No. PCT/EP2017/081987, filed on Dec. 8, 2017, which claims the benefit of Danish Application No. PA 2016 00750, filed on Dec. 8, 2016. The entire contents of each of U.S. application Ser. No. 16/332,600, International Application No. PCT/EP2017/081987, and Danish Application No. PA 2016 00750 are hereby incorporated herein by reference in their entirety.

TECHNICAL FIELD

The present invention relates to a process for the production of glycolaldehyde by thermolytic fragmentation of a carbohydrate feedstock comprising mono- and/or di-saccharide(s) and a system suitable for performing the process. The process and the system are suitable for industrial application, and the process may be performed in a continuous process.

BACKGROUND

In recent years, increased efforts have focused on producing commercial chemicals from renewable feedstocks, such as biomass or sugars. Biomass, and sugars derived therefrom, are of particular interest due to its potential for supplementing, and possibly replacing, fossil resources as a feedstock for the preparation of commercial chemicals. Carbohydrates represent a large fraction of biomass and various strategies for their efficient use as a feedstock for the preparation of commercial chemicals are being established. These strategies include fermentation-based processes, thermolytic fragmentation, and different catalyst-based processes.

The conversion of biomass substrates by high temperature processes is desirable due to the high volumetric production rates which can be achieved, and the ability of these types of processes to convert a wide range of substrates. However, current processes typically have rather low selectivity towards any particular compound, which can be problematic for industrial production of chemicals.

One of the products formed from biomass under pyrolysis conditions is glycolaldehyde (hydroxyacetaldehyde). Glycolaldehyde is the smallest compound containing both a hydroxy and a carbonyl group, thus making it structurally identical to a sugar. It typically constitutes only a relatively small fraction of the products formed from biomass under pyrolysis conditions and furthermore, due to the difficulty in separating it from pyrolysis mixtures, this production method is not economically viable.

It is known that high purity sugars can be fragmented to a $C_1$-$C_3$ oxygenate mixture in a fluidized bed.

U.S. Pat. No. 7,094,932 (Majerski) thus describes a method of producing a food browning ingredient by thermolytic fragmentation of an aqueous solution of glucose or sucrose into glycolaldehyde in a dense fluidized bed of sand particles (also referred to as a bubbling bed). When the feedstock comprises glucose, the yields of glycolaldehyde in the condensed liquid fragmentation product are on mass basis at least 50% by weight of glucose fed to the reactor. The liquid fragmentation product comprises $C_1$-$C_3$ oxygenate compounds including formaldehyde, glycolaldehyde, glyoxal, pyruvaldehyde and acetol. The main product of this reaction is glycolaldehyde, and water is the solvent of the reaction.

U.S. Pat. No. 5,397,582 (Underwood) describes a method for preparation of liquid 'smoke' for browning foodstuffs by injecting sugar, starch, or mixtures thereof into two types of gas-solid contact reactors. The reported yields of glycolaldehyde (oxygenate) are significantly lower compared to Majerski.

Christian Mårup Osmundsen, Catalytic conversion of carbohydrates, Ph.D. thesis (2013), Department of Physics, Technical University of Denmark describes a process for converting monosaccharides by high temperature thermolysis (thermolytic fragmentation) with high selectivity towards $C_1$-$C_3$ oxygenates through thermal retro-aldol condensations. Glycolaldehyde was shown to be prepared in yields above 60%.

The above references have succeeded in obtaining yields of glycolaldehyde above 50 wt % only when using highly refined sugars as substrate (feedstock) for the pyrolysis.

Several references relate to purification of raw or refined sugar. US patent appl. no. 2010/0160624 discloses a process for the purification of raw or refined sugar to produce sucrose and sucrose-related products having substantially no inorganic impurities using ion-exchange technology. U.S. Pat. No. 2,564,820 discloses a process for mixed bed purification of sugar. GB pat. appl. no. 616278 A discloses a process for removal of impurities of an organic nature from aqueous solutions of sugars including treatment with a cation exchanging substance and subsequently an anion exchanging substance. GB pat. appl. no. 633552 A discloses a process for purifying an aqueous sugar solution having an ash content not greater than 0.9% including passage through a system containing a plurality of pairs of ion exchangers, one member of each pair being a cation exchanger and the other member being an anion exchanger.

Although high purity (refined or purified) sugars are commercially available, these are typically sold in powdered form, i.e. an energy intensive and costly crystallization step is required in their purification. Using crude carbohydrate materials, such as sugar syrups, as a carbohydrate feedstock would be significantly cheaper, however these typically contain a number of impurities, such as ash, sulfates, proteins, salts, and oligosaccharides. For second generation sugars, i.e. sugars which have been produced from the inedible part of plant biomass, an even wider range of impurities are present, such as furanics and various organic acids. Many of these compounds are known to cause problems for conventional biomass conversion processes, e.g. furanics and low pH are toxic to microorganisms, while sulfur is known to poison a wide variety of catalysts.

The processes used for refining crude sugars into different grades (purities) of sugar are highly dependent on the nature of the impurities present, which will depend on the type of biomass from which the sugar is derived.

When raw cane sugar is the raw product for producing refined sugar, the raw cane sugar is typically supplied to the sugar refinery as a crystalline product. The crystals themselves are relatively pure (>99%), however they are coated in a film of molasses with a much lower purity (<65%). Thus, the first refining step is removing this film, and thereby the majority of the impurities. This is done by washing the crystals with a near saturated sugar syrup; a process known as affination.

The washed sugar crystals are then dissolved in water, and suspended solids and colloids are removed either by filtration or chemical clarification. The latter is for example performed by adding phosphoric acid and lime. This causes impurities to flocculate, however the floc is not easily removed by filtration, and instead air flotation is typically used to remove the floc by skimming the surface of the liquid.

The next step of the sugar refining is the removal of color from the sugars. The color of the sugar is one of the most important specifications of the final product. The color of raw sugar is caused by a range of different impurities, such as phenolics, melanoidins, caramel and various degradation products. These impurities are typically removed by passing the sugar solution through a bed of an adsorbent, such as activated carbon, bone char, and/or ion-exchange resins.

The final step in the refinery is the recovery of the refined sugar. The sugar solution is heated at reduced pressure to evaporate water, and thus allow the sugar to precipitate as crystals. The crystals are then isolated from the remaining liquid by centrifugation and dried, e.g. in a fluidized bed or rotary drier.

Obviously all of these steps in refining of crude sugars require significant energy and capital expenditure. Furthermore, a loss of sugar must be expected in each step; for instance, approx. 10% of the solids in the crude sugar is used for the affination syrup. Although part of this can be recovered and/or re-used in other parts of the refinery, obviating these steps will be a significant improvement to the production of glycolaldehyde and the other products of the thermolytic fragmentation, since it will simplify the pre-processing of the raw material and thus reduce the costs associated with the production of glycolaldehyde from raw sugar.

However, the prior art has only succeeded in obtaining high yields of glycolaldehyde with refined or purified sugar solutions as carbohydrate feedstock for the thermolytic fragmentation.

Thus, there is a need for a process for production of glycolaldehyde from a carbohydrate feedstock which is industrially applicable and more energy efficient and less costly than the known processes, which are based on converting refined sugar, yet providing a high yield of glycolaldehyde.

SUMMARY

Experiments by the present inventors have shown that when a crude carbohydrate material comprising mono- and/or di-saccharide(s) is used as feedstock for thermolytic fragmentation, the yield of glycolaldehyde is lower than that obtained with a feedstock of high purity sugar. However, as described above the process of obtaining a high purity sugar feedstock from a crude carbohydrate material is energy intensive and costly. If the selectivity towards glycolaldehyde during thermolytic fragmentation (and thus the yield of glycolaldehyde) could be increased even though a crude carbohydrate material was used as carbohydrate feedstock, then thermolytic fragmentation could prove to be a simple process for large scale production of glycolaldehyde, which would allow for the production of commodity chemicals starting from glycolaldehyde.

It has surprisingly been found by the present inventor(s) that the primary cause of this decreased yield when using a crude carbohydrate feedstock (i.e. a carbohydrate feedstock containing a crude carbohydrate material) is not the presence of all of the common impurities, such as proteins, oligosaccharides, caramel, organic acids or furanics, but rather the presence of salts. The present inventors have found that by removing this impurity of salts, for example by an ion exchange procedure, the yield can be increased to the same level as observed for a high purity sugar as carbohydrate material. It is surprising that the salt appears to have a negative effect on the yield of glycolaldehyde using a carbohydrate feedstock comprising mono- and/or di-saccharide, especially as previous investigations of the effect of salts have shown a significant beneficial effect of salt on the yield of glycolaldehyde during polysaccharide pyrolysis (Patwardhan, P., Satrio, J., Brown, R. & Shanks, B. Influence of inorganic salts on the primary pyrolysis products of cellulose. Bioresource technology 101, 4646-55 (2010)).

So, in a first aspect the present invention relates to a process for the production of glycolaldehyde comprising the step of thermolytic fragmentation of a salt-depleted carbohydrate feedstock comprising mono- and/or di-saccharide(s) and less than 200 ppm salts to obtain the glycolaldehyde.

In a second aspect the present invention relates to a process for the production of glycolaldehyde from a crude carbohydrate material comprising mono- and/or di-saccharide(s), said process comprising the steps of:
  removing salt from said crude carbohydrate material, to provide a salt-depleted carbohydrate feedstock comprising less than 200 ppm salts;
  performing thermolytic fragmentation on the salt-depleted carbohydrate feedstock so as to provide glycolaldehyde.

In yet another aspect, the present invention relates to thermolytic fragmentation of a salt-depleted carbohydrate feedstock comprising mono- and/or di-saccharide(s) and less than 200 ppm salts, said process including the step of removing salt from a crude carbohydrate feedstock, prior to said thermolytic fragmentation.

In a further aspect, the present invention relates to the use of a carbohydrate feedstock comprising mono- and/or di-saccharide(s) and less than 200 ppm salts in thermolytic fragmentation for producing glycolaldehyde.

Unless otherwise specified, ppm is meant to refer to parts per million on a weight basis.

In a further aspect, the present invention relates to a system for continuously performing the process as disclosed herein, said system comprising an ion-exchange unit having an inlet and an outlet, and a thermolytic fragmentation unit having inlet and outlet, wherein the outlet of said ion-exchange unit is fluidly connected to the inlet of said thermolytic fragmentation unit.

In a further aspect, the present invention relates to a process for the preparation of ethylene glycol from a carbohydrate feedstock comprising mono- and/or di-saccharide (s), the process comprising carrying out the steps for the production of glycolaldehyde as disclosed herein to obtain a fragmentation product;
  and then subjecting the fragmentation product to a hydrogenation step to obtain ethylene glycol. The fragmentation product may be subjected to purification prior to the hydrogenation step. After hydrogenation the ethylene glycol may be purified.

DETAILED DESCRIPTION

Disclosed herein is a process for the production of glycolaldehyde comprising the step of thermolytic fragmentation of a salt-depleted carbohydrate feedstock comprising mono- and/or di-saccharide(s) and less than 200 ppm salts to obtain the glycolaldehyde.

In a further embodiment disclosed herein, a process for the production of glycolaldehyde comprising the step of thermolytic fragmentation of a salt-depleted carbohydrate feedstock comprising more than 20 wt/wt % mono- and/or di-saccharide(s) and less than 200 ppm salts to obtain the glycolaldehyde, is disclosed.

As disclosed herein the salt-depleted carbohydrate feedstock comprises less than 200 ppm salts. As used herein the term "salts" refers to one or more compounds which consist of positive and negative ions, for example $Na^+$ and $Cl^-$ in NaCl. Other examples of salts are KCl, CsCl, $CaCl_2$, CsF, $KClO_4$ $NaNO_3$, $CaSO_4$, and Na (acetate) composed of (positive) cations and (negative) anions. The amount of salts in ppm may be measured by elemental analysis, such as by inductively coupled plasma optical emission spectroscopy (ICP-OES) or by other methods known to a person skilled in the art. In one embodiment, the salts are measured by inductively coupled plasma optical emission spectroscopy (ICP-OES).

In an embodiment disclosed herein, the process comprises a step of salt-depleting a crude carbohydrate feedstock prior to thermolytic fragmentation to obtain a salt-depleted carbohydrate feedstock comprising less than 200 ppm salts.

In an embodiment disclosed herein, the prior step of salt-depleting a crude carbohydrate feedstock is conducted by means of ion-exchange. The ion-exchange may be performed by mixing the crude carbohydrate feedstock with a suitable ion-exchange resin. Alternatively, the crude carbohydrate feedstock may be passed through a bed of a suitable ion-exchange resin. The ion-exchange resin must be selected based on the salts, and possibly other species, present in the crude carbohydrate mixture, but will typically be a mixture of an anion-exchange resin and a cation-exchange resin. An example of a suitable ion-exchange resin is DOWEX MB mixed ion exchange resin, which is a 1:1 equivalent mixture of strong acid cation and strong base anion exchange resins.

As used herein, the term "carbohydrate feedstock" refers to a carbohydrate solution for feeding to a thermolytic fragmentation unit which includes mono- and/or di-saccharide(s) as carbohydrates. It is preferably an aqueous solution.

As used herein, the term "crude carbohydrate material" refers to a carbohydrate raw material which includes mono- and/or di-saccharide(s) and which is obtained, in whole or in significant part, from biological products or renewable agricultural materials (including, but not limited to, plant, animal and marine materials) or forestry materials and which may be in the form of a solution, by extraction or hydrolysis of the products or materials without further purifying or refining the solution. The crude carbohydrate feedstock may be obtained from extraction and/or hydrolysis of e.g. potato, wheat, corn, sugar cane, sorghum, sugar beets, wood; or a mixture thereof. Exemplary crude carbohydrate materials are cane sugar, cane sugar syrup, sugar maple syrup, cellulose hydrolysate, starch hydrolysate, hemi-cellulose hydrolysate, corn syrup, and sugar beet syrup. In the present context trivial processes such as sieving/filtration to remove solid matter and evaporation to reduce water content is not considered further purifying or refining the solution. Further purifying or refining is only meant to refer to subjecting the crude carbohydrate material to unit operations to reduce the amount of unwanted substances, such as salts, proteins, caramels etc.

In an embodiment, the crude carbohydrate material is in solution.

As used herein, the term "salt-depleted carbohydrate feedstock" refers to a carbohydrate feedstock which feedstock has been obtained from a crude carbohydrate material which has been subjected to a salt depletion step to reduce the concentration of salts significantly, in particular to below 200 ppm. In a salt-depleted carbohydrate feedstock the crude carbohydrate material has not been subjected to a complete purification or refining. Preferably, the crude carbohydrate material has not been subjected to unit operations (e.g. purification or refining operations) to reduce the level of impurities other than the salt depletion step.

As used herein, the term "refined or purified sugar" refers to a sugar (carbohydrate) which has been subjected to purification steps to reduce the content of one or more of the impurities selected from proteins, insolubles, caramels, acids, furanics. The sugar has possibly also been subjected to a salt reduction step.

Typically, the crude carbohydrate material comprises more than 250 ppm salts, such as more than 300 ppm salts, such as more than 500 ppm salts, such as more than 800 ppm salts, such as more than 1,000 ppm salts, such as more than 5,000 ppm salts, such as more than 10,000 ppm salts, such as more than 20,000 ppm salts. In an embodiment, the crude carbohydrate material comprises between 250 ppm-50,000 ppm salts, such as between 250 ppm-10,000 ppm salts, such as between 250 ppm-5,000 ppm salts, such as between 250 ppm-1,500 ppm salts.

In an embodiment, the crude carbohydrate material is selected from cane sugar, cane sugar syrup, sugar maple syrup, cellulose hydrolysate, starch hydrolysate, hemi-cellulose hydrolysate, corn syrup, sugar beet syrup; or a mixture thereof. The syrups or hydrolysates may be obtained by extracting the saccharides from the raw materials or from hydrolyzing the polysaccharides of the raw materials.

Thus in an embodiment disclosed herein, the crude carbohydrate material need only be subjected to a step of salt-depletion prior to exposing it to thermolytic fragmentation in order to obtain yields suitable for industrial application. Yields obtainable by the method according to the present invention may be as high as above 50%, such as above 60, 66 or 70% (based on carbon/carbon). In another embodiment, the crude carbohydrate material may also be subjected to further steps such as filtration and/or clarification before or after salt-depletion.

In an embodiment disclosed herein, the crude carbohydrate material is defined by its color and has a color above 75 ICUMSA units (IU), such as above 80 ICUMSA units, such as above 85 ICUMSA units, such as above 100 ICUMSA units, such as above 200 ICUMSA units, such as above 400 ICUMSA units, such as above 600 ICUMSA units, such as above 800 ICUMSA units, such as above 1000 ICUMSA units, such as above 1200 ICUMSA units. In an embodiment disclosed herein, the salt-depleted carbohydrate feedstock has a color between 75-30000 ICUMSA units, such as between 80-25000 ICUMSA units, such as between 100-25000 ICUMSA units.

In an embodiment, the crude carbohydrate material comprises one or more impurities selected from the group of arsenic, lead, sulfate, sulfur dioxide, and 5-(hydroxymethyl) furfural.

In a further embodiment disclosed herein, the crude carbohydrate material comprises one or more of the following impurities in the specified amount:
sulfate: >0.025 wt/wt %, such as above 0.035 wt/wt %, such as above 0.050 wt/wt % sulfur dioxide: >0.002 wt/wt %, such as above 0.003 wt/wt %, such as above 0.004 wt/wt %

5-(hydroxymethyl)furfural: >0.1 wt/wt %, such as above 0.2 wt/wt %, such as above 0.3 wt/wt Arsenic: >1 mg/kg, such as above 2 mg/kg, such as above 3 mg/kg Lead: >0.1 mg/kg, such as above 0.2 mg/kg, such as above 0.3 mg/kg.

The above mentioned impurities and color of the crude carbohydrate material may be measured as described below.

An advantage of the process disclosed herein is that the salt-depleted carbohydrate feedstock used in the fragmentation process may comprise one or more impurities which is typically removed when refining sugar, and thereby avoiding many if not all of the steps in refining of crude sugars otherwise requiring significant energy and capital expenditure.

In an embodiment disclosed herein, the salt-depleted carbohydrate feedstock is defined by its color and has a color above 75 ICUMSA units (IU), such as above 80 ICUMSA units, such as above 85 ICUMSA units, such as above 100 ICUMSA units, such as above 200 ICUMSA units, such as above 400 ICUMSA units, such as above 600 ICUMSA units, such as above 800 ICUMSA units, such as above 1000 ICUMSA units, such as above 1200 ICUMSA units. In an embodiment disclosed herein, the salt-depleted carbohydrate feedstock has a color between 75-30000 ICUMSA units, such as between 80-25000 ICUMSA units, such as between 100-25000 ICUMSA units.

The color of a carbohydrate sample may be measured in ICUMSA units by preparing a 50 wt/wt % solution of the carbohydrate sample and adjusting the pH to 7 by addition of sodium hydroxide or hydrochloric acid. The solution is then filtered to remove insoluble solids and obtain a clear solution. The absorbancy of the solution is measured on a spectrophotometer at 420 nm. The color of the sugar may then be calculated in ICUMSA units by the following formula:

$$IU = A_s/(b\ c) \times 1000$$

where $A_s$ is the measured absorbancy, b is the cell length in cm, and c is the total solids concentration in g/mL.

As also disclosed herein the salt-depleted carbohydrate feedstock comprises mono- and/or di-saccharide(s).

In an embodiment disclosed herein, the mono- and/or di-saccharide(s) is selected from the group consisting of sucrose, lactose, maltose, xylose, arabinose, ribose, mannose, tagatose, galactose, glucose and fructose or mixtures thereof. In a further embodiment, the monosaccharide(s) is selected from the group consisting of glucose, galactose, tagatose, mannose, fructose, xylose, arabinose, ribose or mixtures thereof. In an embodiment, the salt-depleted carbohydrate feedstock comprises both monosaccharides and di-saccharides.

In an embodiment disclosed herein, the salt-depleted carbohydrate feedstock for fragmentation comprises more than 20 wt/wt %, more than 30 wt/wt %, more than 40 wt/wt %, more than 50 wt/wt %, more than 60 wt/wt %, more than 70 wt/wt %, more than 80 wt/wt %, more than 90 wt/wt %, such as between 20-90 wt/wt %, between 30-90 wt/wt %, or between 50-90 wt/wt % mono- and/or di-saccharide(s). In an embodiment disclosed herein, the salt-depleted carbohydrate feedstock for fragmentation comprises more than 20 wt/wt %, more than 30 wt/wt %, more than 40 wt/wt %, more than 50 wt/wt %, more than 60 wt/wt %, more than 70 wt/wt %, more than 80 wt/wt %, more than 90 wt/wt %, such as between 20-90 wt/wt %, between 30-90 wt/wt %, or between 50-90 wt/wt % mono-saccharide(s).

In an embodiment as disclosed herein, the pH of the salt-depleted carbohydrate feedstock is below 6, such as between pH 2-6, such as between pH 3-6, such as between pH 4-6.

In an embodiment disclosed herein, the salt-depleted carbohydrate feedstock comprises one or more impurities selected from the group of arsenic, lead, sulfate, sulfur dioxide, and 5-(hydroxymethyl)furfural.

In a further embodiment disclosed herein, the salt-depleted carbohydrate feedstock comprises one or more of the following impurities in the specified amount:

sulfate: >0.025 wt/wt %, such as above 0.035 wt/wt %, such as above 0.050 wt/wt % sulfur dioxide: >0.002 wt/wt %, such as above 0.003 wt/wt %, such as above 0.004 wt/wt %

5-(hydroxymethyl)furfural: >0.1 wt/wt %, such as above 0.2 wt/wt %, such as above 0.3 wt/wt %

Arsenic: >1 mg/kg, such as above 2 mg/kg, such as above 3 mg/kg

Lead: >0.1 mg/kg, such as above 0.2 mg/kg, such as above 0.3 mg/kg.

The amount of these impurities may be measured by methods known to the persons skilled in the art. For instance, sulfate may be measured by ion-chromatography, sulfur dioxide may be measured by titration, 5-(hydroxymethyl)furfural may be measured by liquid chromatography, and arsenic and lead may be measured by inductively couple plasma optical emission spectroscopy (ICP-OES).

In a further embodiment disclosed herein, the salt-depleted carbohydrate feedstock comprises a total amount of heavy metals of more than 5 mg/kg, such as above 10 mg/kg. The total amount of heavy metals of the salt-depleted carbohydrate feedstock may be measured by inductively couple plasma optical emission (ICP-OES).

In a further embodiment disclosed herein, the salt-depleted carbohydrate feedstock has an ash content above 0.5 wt/wt %, such as above 1.0 wt/wt %, measured as gravimetric (or sulfated) ash. The gravimetric (or sulfated) ash may be determined as described in "Cane Sugar Handbook" (J. P. C. Chen and C. C. Chou, 12$^{th}$ ed., Wiley). Briefly, an appropriate amount of sample is placed in a crucible and an equivalent amount of sulfuric acid is added. The mixture is heated gently until the sample has been carbonized. The sample is then heated to 550° C. in a muffle furnace until apparently free of carbon. The sample is cooled to room temperature and rewetted with sulfuric acid, and then heated to 650° C. in a muffle furnace to constant weight. The ash content may then be determined as the weight of residual mass divided by the original sample mass.

In a further embodiment disclosed herein, the salt-depleted carbohydrate feedstock has an ash content above 0.5 wt/wt %, such as above 1.0 wt/wt %, measured as conductivity ash. The conductivity ash may be determined as described in "Cane Sugar Handbook" (J. P. C. Chen and C. C. Chou, 12$^{th}$ ed., Wiley). Briefly, 28.0 g of sample is dissolved in 72.0 g of deionized water. The conductivity of the solution is measured at 20° C. The measured conductivity is corrected for the conductivity of the water using the following formula:

$$C = C_{as\ read} - 0.35 C_{Water}$$

Based on empirical correlations, the conductivity ash can now be calculated by the following formula:

Conductivity ash [in wt/wt %]=6·10$^{-4}$ C [in μS/cm]

There are several existing specifications for food grade sugar-containing materials, which outline the limits of typical impurities. One example is the Food Chemicals Codex, FCC, (US Pharmacopeial Convention) which provide guidelines for impurities in food additives. The specifications given are only for impurities commonly observed in the additive, and it is therefore not an exhaustive list which guarantees that the additive is suitable for human consumption. In addition to the listed specifications, the product must live up to good manufacturing practice (GMP). The FCC lists specifications for sugar materials such as glucose, fructose, sucrose, invert sugar, and glucose syrup, all of which may be prepared from multiple raw materials. The limits for the different materials are not identical, both because some impurities are only commonly observed in certain materials (i.e. 5-(hydroxymethyl)furfural is only commonly observed in invert sugar) and because some impurities are not related to food safety (i.e. fructose should contain less than 0.5% glucose). In general, sugar-containing materials should live up to the following specifications to be considered food grade under the FCC:

Arsenic: <1 mg/kg
Lead: <0.1 mg/kg
Heavy metals: <5 mg/kg
Sulfate: <0.025%
Sulfur dioxide: <0.002%
5-(Hydroxymethyl)furfural: <0.1%
Color: <75 IU
Residue on ignition: <0.5%

In a further embodiment disclosed herein, the salt-depleted carbohydrate feedstock is of non-food grade purity as defined by the Food Chemicals Codex.

Other impurities, which are not listed in the FCC, but which must obviously be removed for food grade applications are parasites, larvae, mites, bacteria and other extraneous matter, such as sand or similar. Depending on the equipment used for example for thermolytic fragmentation, these impurities may also be removed when performing the herein disclosed process.

In an embodiment disclosed herein, the salt-depleted carbohydrate feedstock is injected into a thermolytic fragmentation unit in the form of an aqueous solution.

In general, thermal fragmentation of sugars to smaller oxygenates, primarily $C_1$-$C_3$ oxygenates, can be performed at high temperatures. In order to avoid side-reactions, a very high heating rate is usually required, thus a suitable means for performing the reaction is a fluid bed reactor. In this type of reactor, the rapid mixing of the bed material leads to a near isothermal temperature profile over the bed, which allows for rapid heating of the feed. A fluidized bed reactor is a reactor which accommodates a bed of particles to be fluidized by a fluidization gas stream which is usually introduced at the bottom of the reactor. The velocity and physical properties of the fluidization gas stream combined with the physical properties of the particles regulates the fluidization state of the particles within the bed. A dense bed/turbulent bed/bubbling bed is usually considered having a superficial velocity of the fluidization gas stream within the reactor of 0.1-2 m/s.

If the substrate (feedstock) is further introduced in the form of small droplets, i.e. as an aqueous solution injected through an atomization nozzle, an even higher heating rate can be achieved due to the high surface area of the feed upon injection. This has the further advantage that a high degree of dispersion of the substrate is achieved in the reactor, minimizing intermolecular reactions, which would otherwise reduce the selectivity to the desired $C_1$-$C_3$ oxygenates.

Accordingly, another suitable means for performing the thermal fragmentation reaction is by means of a bubbling fluid bed reactor, which is fluidized using an inert gas, such as nitrogen. The bed material is preferably an inert material, such as sand or glass beads, which is maintained at the desired reaction temperature, e.g. 400-800° C. Under certain circumstances the reaction temperature may be in the range of from 350-800° C. The substrate (feedstock) is pumped to the reactor, preferably as an aqueous solution, and injected into the bed through a suitable nozzle to achieve a high dispersion of the feed, e.g. a two-fluid nozzle capable of atomizing the feed to droplets smaller than 50 μm. In this way, the required very high heating rate of the feed may be achieved, allowing for a high selectivity to the desired $C_1$-$C_3$ oxygenates. At these reaction conditions, the desired oxygenates are in the gas phase and will therefore be carried out of the reactor with the fluidization gas; they are however not stable at the reaction conditions and it is therefore preferable that a low residence time in the reactor is obtained. After the gaseous product has exited the reactor it may be sent to downstream process steps, such as a condensation step to collect the $C_1$-$C_3$ oxygenates as an aqueous solution.

In a further embodiment disclosed herein, the thermolytic fragmentation unit is a fluidized bed reactor, such as a riser reactor.

In an embodiment, the fluid bed reactor is a fast fluidized bed reactor (or a riser/transport reactor). A fast fluidized bed reactor is usually considered to have a superficial velocity of fluidization stream within the reactor of 3-22 m/s. The exact velocity range is however dependent on the physical properties of the particles and fluidization gas and can be determined experimentally or calculated by a person skilled in the art.

In general, the riser is a vertically extending reactor, which in the lower part comprises a fluidization stream inlet, a particle inlet and a feedstock inlet, and wherein the particle inlet is provided downstream the fluidization inlet, and the feedstock inlet is provided downstream the particle inlet. For the purpose of the present invention, the particles may form a dense phase fluidized bed in the zone between the particle inlet and the feedstock inlet. The fluidization stream and thus the fluidization stream inlet could be dispensed with. For example, the feedstock could be introduced right after the heat carrying particles and thus serve as fluidization stream.

The temperature of the particles at the particle inlet of the fragmentation reactor is preferably at least 300° C., such as at least 400, 450, 500, 550, 600 or 650° C. Preferably, the temperature of the particles at the particle inlet is within the range of from 300-800° C., such as in the range of from 400-800 or 450-650° C.

The feedstock may be introduced at any point after introducing the heat carrying particles. When the feedstock meets the heat carrying particles, a vaporisation zone is formed in which the solvent evaporates and gaseous products starts to be generated from the sugar fragmentation. This results in an increase in the superficial velocity of the gas thereby entraining the heat carrying particles. Accordingly, downstream the feedstock inlet, the heat carrying particles and the feedstock form a fast bed above the vaporisation zone, which may be referred to as a riser. According to an embodiment of the present invention, the feedstock inlet is provided in the lower part of the riser.

Using a riser reactor has the advantages of facilitating high energy transfer rate and quick separation of fragmentation product and heat carrier.

The bed material is preferably selected from the group consisting of sand, silica, glass, alumina, steel, and silicon carbide.

In a further embodiment, the thermolytic fragmentation is performed at a temperature between 400 and 800° C., such as between 400 and 600° C., preferably between 500 and 600° C. Under certain circumstances the reaction temperature may be in the range of from 350-800° C.

In a further embodiment disclosed herein, the production of glycolaldehyde from a crude carbohydrate material comprising mono- and/or di-saccharide(s), comprises the steps of:
removing salt from said crude carbohydrate material, to provide a carbohydrate feedstock comprising less than 200 ppm salts; performing thermolytic fragmentation on the carbohydrate feedstock so as to provide glycolaldehyde.

In a further embodiment, a process of thermolytic fragmentation of a carbohydrate feedstock comprising mono- and/or di-saccharide(s) and less than 200 ppm salts, said process including the step of removing salt from a crude carbohydrate material, prior to said thermolytic fragmentation, is disclosed.

In a further embodiment, a use of a carbohydrate feedstock comprising mono- and/or di-saccharide(s) and less than 200 ppm salts in thermolytic fragmentation for producing glycolaldehyde, is disclosed.

In a further embodiment, a system for continuously performing the process as disclosed herein, said system comprising an ion-exchange unit having an inlet and an outlet, and a thermolytic fragmentation unit having inlet and outlet, wherein the outlet of said ion-exchange unit is fluidly connected to the inlet of said thermolytic fragmentation unit, is disclosed.

According to an embodiment, the process disclosed herein is operated as a continuous process. This is an advantage for industrial application.

In the present context, the fragmentation product is meant to refer to the stream resulting from the thermolytic fragmentation of the salt-depleted carbohydrate material comprising $C_1$-$C_3$ oxygenates.

In another embodiment, disclosed herein is a process for the preparation of ethylene glycol from a carbohydrate feedstock comprising mono- and/or di-saccharide(s), the process comprising carrying out the steps for the production of glycolaldehyde as disclosed herein to obtain a fragmentation product;
and then subjecting the fragmentation product to a hydrogenation step to obtain ethylene glycol.

In a further embodiment, the carbohydrate feedstock comprises at least 20 wt/wt % mono- and/or di-saccharide(s)

Further embodiments disclosed herein:

Embodiment 1. A process for the production of glycolaldehyde comprising the step of thermolytic fragmentation of a salt-depleted carbohydrate feedstock comprising mono- and/or di-saccharide(s) and less than 200 ppm salts to obtain the glycolaldehyde.

Embodiment 2. A process for the production of glycolaldehyde comprising the step of thermolytic fragmentation of a salt-depleted carbohydrate feedstock comprising at least 20 wt/wt % mono- and/or di-saccharide(s) and less than 200 ppm salts to obtain the glycolaldehyde.

Embodiment 3. The process according to any one of embodiment 1 or 2, wherein the salt-depleted carbohydrate feedstock has a color above 75 ICUMSA units (IU).

Embodiment 4. The process according to any one of preceding embodiments, wherein the salt-depleted carbohydrate feedstock comprises more than 30 wt/wt %, more than 40 wt/wt %, more than 50 wt/wt %, more than 60 wt/wt %, more than 70 wt/wt %, more than 80 wt/wt %, such as between 80-90 wt/wt % mono-saccharide(s).

Embodiment 5. The process according to any one of the preceding embodiments, wherein the salt-depleted carbohydrate feedstock comprises one or more impurities selected from the group of arsenic, lead, sulfate, sulfur dioxide, and 5-(hydroxymethyl)furfural.

Embodiment 6. The process according to any one of the preceding embodiments, wherein the salt-depleted carbohydrate feedstock comprises a total amount of heavy metals of more than 5 mg/kg.

Embodiment 7. The process according to any one of the preceding embodiments, wherein the salt-depleted carbohydrate feedstock has a residue on ignition above 0.5 wt/wt %.

Embodiment 8. The process according to any one of the preceding embodiments, wherein the pH of the salt-depleted carbohydrate feedstock is below 6.

Embodiment 9. The process according to any one of the preceding embodiments, wherein the salt-depleted carbohydrate feedstock comprises one or more of the following impurities in the specified amounts
sulfate: >0.025 wt/wt %
sulfur dioxide: >0.002 wt/wt %
5-(hydroxymethyl)furfural: >wt/wt 0.1%
Arsenic: >1 mg/kg and/or
Lead: >0.1 mg/kg.

Embodiment 10. The process according to any one of the preceding embodiments, wherein the salt-depleted carbohydrate feedstock is of non-food grade purity as defined by the Food Chemicals Codex.

Embodiment 11. The process according to any one of the preceding embodiments, wherein the process comprises a prior step of salt-depleting a crude carbohydrate material to obtain a salt-depleted carbohydrate feedstock comprising less than 200 ppm salts.

Embodiment 12. The process according to embodiment 11, wherein the crude carbohydrate material is salt-depleted by means of ion-exchange.

Embodiment 13. The process according to any one of embodiments 11 or 12, wherein the crude carbohydrate material is selected from cane sugar syrup, cellulose hydrolysate, starch hydrolysate, hemi-cellulose hydrolysate, corn syrup, sugar beet syrup; or a mixture thereof.

Embodiment 14. The process according to any one of the preceding embodiments, wherein the mono- and/or di-saccharide(s) is selected from the group consisting of sucrose, lactose, maltose, xylose, arabinose, ribose, mannose, tagatose, galactose, glucose and fructose; or mixtures thereof.

Embodiment 15. The process according to any one of the preceding embodiments, wherein the monosaccharide(s) is selected from the group consisting of glucose, galactose, tagatose, mannose, fructose, xylose, arabinose, ribose; or mixtures thereof.

Embodiment 16. The process according to any one of the preceding embodiments, wherein the salt-depleted carbohydrate feedstock comprises less than 180 ppm, less than 170 ppm, less than 160 ppm, less than 150 ppm, less than 140 ppm, less than 50 ppm salts.

Embodiment 17. The process according to any one of the preceding embodiments, wherein the salt-depleted carbohydrate feedstock is injected into a thermolytic fragmentation unit in the form of an aqueous solution.

Embodiment 18. The process according to any one of the preceding embodiments, wherein the thermolytic fragmentation unit comprises a fluidized bed reactor.

Embodiment 19. The process according to any one of the preceding embodiments, wherein the thermolytic fragmentation is performed at a temperature between 400 and 600° C.

Embodiment 20. A process for the production of glycolaldehyde from a crude carbohydrate material comprising mono- and/or di-saccharide(s), said process comprising the steps of:
  a. removing salt from said crude carbohydrate material, to provide a salt-depleted carbohydrate feedstock comprising less than 200 ppm salts;
  b. performing thermolytic fragmentation on the salt-depleted carbohydrate feedstock so as to obtain glycolaldehyde.

Embodiment 21. A process for the production of glycolaldehyde from a crude carbohydrate material comprising at least 20 wt/wt % mono- and/or di-saccharide(s), said process comprising the steps of:
  a. removing salt from said crude carbohydrate material, to provide a salt-depleted carbohydrate feedstock comprising less than 200 ppm salts;
  b. performing thermolytic fragmentation on the salt-depleted carbohydrate feedstock so as to obtain glycolaldehyde.

Embodiment 22. The process according to any one of embodiment 20 or 21, wherein removing salt from said crude carbohydrate material is by means of ion-exchange.

Embodiment 23. A process of thermolytic fragmentation of a salt-depleted carbohydrate feedstock comprising mono- and/or di-saccharide(s) and less than 200 ppm salts, said process including the step of removing salt from a crude carbohydrate material, prior to said thermolytic fragmentation.

Embodiment 24. A process of thermolytic fragmentation of a salt-depleted carbohydrate feedstock comprising at least 20 wt/wt % mono- and/or di-saccharide(s) and less than 200 ppm salts, said process including the step of removing salt from a crude carbohydrate material, prior to said thermolytic fragmentation.

Embodiment 25. A process for the preparation of a $C_1$-$C_3$ hydroxy compound from a carbohydrate feedstock comprising mono- and/or di-saccharide(s), the process comprising carrying out the steps for the production of glycolaldehyde according to any one of embodiments 1-24 to obtain a fragmentation product;
  and then subjecting the fragmentation product to a hydrogenation to obtain ethylene glycol.

Embodiment 26. A process for the preparation of a $C_1$-$C_3$ hydroxy compound from a carbohydrate feedstock comprising at least 20 wt/wt % mono- and/or di-saccharide(s), the process comprising carrying out the steps for the production of glycolaldehyde according to any one of embodiments 1-24 to obtain a fragmentation product;
  and then subjecting the fragmentation product to a hydrogenation to obtain ethylene glycol.

Embodiment 27. Use of a carbohydrate feedstock comprising mono- and/or di-saccharide(s) and less than 200 ppm salts in thermolytic fragmentation for producing glycolaldehyde.

Embodiment 28. Use of a carbohydrate feedstock comprising at least 20 wt/wt % mono- and/or di-saccharide(s) and less than 200 ppm salts in thermolytic fragmentation for producing glycolaldehyde.

Embodiment 29. A system for continuously performing the process according to any one of embodiments 1-26, said system comprising an ion-exchange unit having an inlet and an outlet, and a thermolytic fragmentation unit having inlet and outlet, wherein the outlet of said ion-exchange unit is fluidly connected to the inlet of said thermolytic fragmentation unit.

EXAMPLES

Example 1

Glucose was fragmented to a $C_1$-$C_3$ oxygenate mixture by the following procedure: A fluidized bed with an inner diameter of 41 mm was loaded with 50 ml of glass beads. The bed was fluidized with nitrogen and heated to 510° C. A 20 wt/wt % aqueous solution of glucose was prepared from glucose (VWR Chemicals) and injected into the fluid bed at a rate of 2 g/min. The feed was injected using a two-fluid nozzle to deliver the feed as a fine mist into the bed. The superficial gas velocity in the reactor at reaction conditions was approx. 40 cm/s. The gas stream leaving the reactor was immediately cooled to 1° C. using a surface condenser to separate the liquid product from the permanent gasses. The liquid product was collected and the concentration of $C_1$-$C_3$ oxygenates quantified by HPLC analysis.

Figure 1:
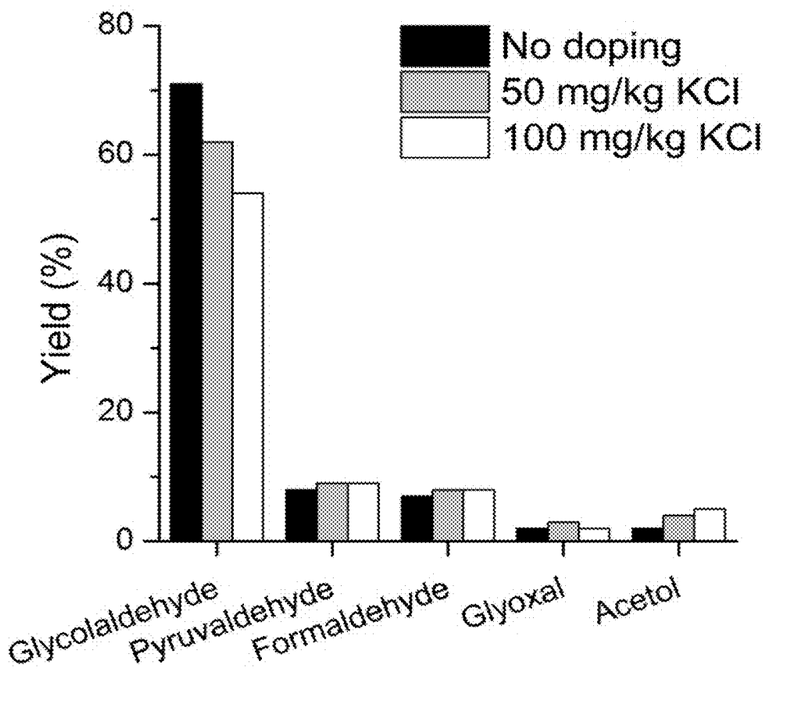
FIG. 1 shows a correlation between the concentration of KCl in a carbohydrate feed of glucose and the yield of glycolaldehyde.

To investigate the effect of content of salts in the feed, a series of experiments was performed with increasing levels of KCl added to the feed. The content of salts in the glucose was determined by elemental analysis using ICP-OES. The total content of KCl was below 10 mg/kg (10 ppm), meaning that the content of KCl in the feed without doping was below 2 mg/kg (2 ppm). FIG. 1 depicts the yield of oxygenates obtained from the fragmentation of glucose at 510° C., with different levels of KCl in the feed. The reported yields are the carbon yields of the various products with respect to the amount of glucose fed to the reactor. As can be seen in FIG. 1 within the studied concentration range there is a direct correlation between the concentration of KCl in the feed and the yield of glycolaldehyde, with smaller amounts of KCl being preferable. Interestingly, it appears that the detrimental effect of KCl in the feed is most pronounced for glycolaldehyde.

The invention claimed is:

1. A process for the production of glycolaldehyde comprising the step of thermolytic fragmentation of a salt-depleted carbohydrate feedstock comprising at least 20 wt/wt % mono- and/or di-saccharide(s) and less than 200 ppm salts to obtain the glycolaldehyde, wherein the salt-depleted carbohydrate feedstock comprises one or more impurities selected from the group consisting of arsenic, lead, sulfate, sulfur dioxide, and 5-(hydroxymethyl)furfural.

2. The process according to claim 1, wherein the salt-depleted carbohydrate feedstock comprises 5-(hydroxymethyl)furfural.

3. The process according to claim 1, wherein the salt-depleted carbohydrate feedstock has a color above 75 ICUMSA units (IU).

4. The process according to claim 1, wherein the salt-depleted carbohydrate feedstock comprises more than 30 wt/wt % mono-saccharide(s).

5. The process according to claim 1, wherein the salt-depleted carbohydrate feedstock comprises a total amount of heavy metals of more than 5 mg/kg.

6. The process according to claim 1, wherein the salt-depleted carbohydrate feedstock has a residue on ignition above 0.5 wt/wt %.

7. The process according to claim 1, wherein the pH of the salt-depleted carbohydrate feedstock is below 6.

8. The process according to claim 1, wherein the salt-depleted carbohydrate feedstock is of non-food grade purity as defined by the Food Chemicals Codex.

9. The process according to claim 1, wherein the process comprises a prior step of salt-depleting a crude carbohydrate material to obtain a salt-depleted carbohydrate feedstock comprising less than 200 ppm salts.

10. The process according to claim 9, wherein the crude carbohydrate material is salt-depleted by means of ion-exchange.

11. The process according to claim 9, wherein the crude carbohydrate material is selected from cane sugar, cane sugar syrup, cellulose hydrolysate, starch hydrolysate, hemicellulose hydrolysate, corn syrup, sugar beet syrup; or a mixture thereof.

12. The process according to claim 1, wherein the salt-depleted carbohydrate feedstock comprises less than 180 ppm salts.

13. The process according to claim 1, wherein the salt-depleted carbohydrate feedstock is injected into a thermolytic fragmentation unit in the form of an aqueous solution.

14. A process for the production of glycolaldehyde from a crude carbohydrate material comprising at least 20 wt/wt % mono- and/or di-saccharide(s), said process comprising the steps of:
  a. removing salt from said crude carbohydrate material, to provide a salt-depleted carbohydrate feedstock comprising less than 200 ppm salts;
  b. performing thermolytic fragmentation on the salt-depleted carbohydrate feedstock so as to obtain glycolaldehyde, wherein the salt-depleted carbohydrate feedstock comprises one or more impurities selected from the group consisting of arsenic, lead, sulfate, sulfur dioxide, and 5-(hydroxymethyl)furfural.

15. The process according to claim 14, wherein the salt-depleted carbohydrate feedstock comprises 5-(hydroxymethyl)furfural.

16. The process according to claim 14, wherein the salt-depleted carbohydrate feedstock is of non-food grade purity as defined by the Food Chemicals Codex.

17. The process according to claim 14, wherein the crude carbohydrate material is selected from cane sugar, cane sugar syrup, cellulose hydrolysate, starch hydrolysate, hemicellulose hydrolysate, corn syrup, sugar beet syrup; or a mixture thereof.

18. The process according to claim 14, wherein removing salt from said crude carbohydrate material is by means of ion-exchange.

19. A system for continuously performing the process according to claim 18, said system comprising an ion-exchange unit having an inlet and an outlet, and a thermolytic fragmentation unit having inlet and outlet, wherein the outlet of said ion-exchange unit is fluidly connected to the inlet of said thermolytic fragmentation unit.

* * * * *